(12) United States Patent
Molina et al.

(10) Patent No.: US 11,723,604 B2
(45) Date of Patent: Aug. 15, 2023

(54) SYSTEM AND METHOD FOR REDUCING PHYSIOLOGICAL DATA SIZE

(71) Applicant: KONINKLIJKE PHILIPS N.V., Eindhoven (NL)

(72) Inventors: Gary Nelson Garcia Molina, Madison, WI (US); Stefan Pfundtner, Eindhoven (NL); Antonio Aquino, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 739 days.

(21) Appl. No.: 16/621,884

(22) PCT Filed: Jun. 13, 2018

(86) PCT No.: PCT/EP2018/065580
§ 371 (c)(1),
(2) Date: Dec. 12, 2019

(87) PCT Pub. No.: WO2018/229090
PCT Pub. Date: Dec. 20, 2018

(65) Prior Publication Data
US 2020/0113522 A1  Apr. 16, 2020

Related U.S. Application Data

(60) Provisional application No. 62/520,102, filed on Jun. 15, 2017.

(30) Foreign Application Priority Data

Aug. 22, 2017 (EP) .................................. 17187349

(51) Int. Cl.
*A61B 5/00* (2006.01)
*H03M 7/30* (2006.01)
*A61B 5/369* (2021.01)

(52) U.S. Cl.
CPC ............ *A61B 5/7232* (2013.01); *A61B 5/369* (2021.01); *A61B 5/4806* (2013.01); *H03M 7/3088* (2013.01)

(58) Field of Classification Search
CPC ................... A61B 5/7232; A61B 5/369; A61B 5/4806–4815; H03M 7/3088; H03M 7/30
See application file for complete search history.

(56) References Cited

U.S. PATENT DOCUMENTS

2008/0238749 A1* 10/2008 Corndorf ................ H03M 7/40
607/60
2016/0256067 A1* 9/2016 Low ...................... A61B 5/7246

OTHER PUBLICATIONS

International Search Report and Written Opinion, International Application No. PCT/EP2018/065580, dated Sep. 6, 2018.
(Continued)

*Primary Examiner* — Scott M. Getzow

(57) ABSTRACT

The present disclosure pertains to systems and methods for encoding and/or decoding brain activity signals for data reduction. In a non-limiting embodiment, first user data associated with a first sleep session of a user is received. The first user data is determined to include at least a first instance of a first sleep feature being of a first data size. A first value representing the first instance during a first temporal interval is determined. First encoding data representing the first value is determine, the first encoding data being of a second data size that is less than the first data size. Second user data is generated by encoding the first user data using the first encoding data to represent the first instance in the second user data, and the second user data is stored.

14 Claims, 10 Drawing Sheets

(56) References Cited

OTHER PUBLICATIONS

Ylöstalo, J. "Data compression methods for EEG", Technology and Healthcare 7, 1999.
J. A. Hobson, "Sleep is of the brain, by the brain and for the brain," Nature, vol. 437, No. 7063, pp. 1254-1256, 2005.
P. R. T. Ko, J. A. Kientz, E. K. Choe, M. Kay, C. A. Landis, and N. F. Watson, "Consumer sleep technologies: A review of the landscape," J. Clin. Sleep Med., vol. 11, No. 12, pp. 1455-1461, 2015.
W. Liu, B. Ploderer, and T. Hoang, "In Bed with Technology: Challenges and Opportunities for Sleep Tracking," in Proceedings of the Annual Meeting of the Australian Special Interest Group for Computer Human Interaction on—OzCHI '15, 2015, pp. 142-151.

\* cited by examiner

400

| Feature | Bits per sample |
|---|---|
| Impedance | 1.7 |
| Beta RMS | 1.8 |
| EEG range | 2.4 |
| Sleep depth | 3.1 |
| Alpha RMS | 2.9 |
| Delta RMS | 3.7 |
| Hypnogram | 2 |
| SW density | 2.5 |
| Detected arousal | 2 |
| SW flag | 3 |
| EEG raw | 2.5 |

FIG. 4

SYSTEM AND METHOD FOR REDUCING PHYSIOLOGICAL DATA SIZE

CROSS-REFERENCE TO PRIOR APPLICATIONS

This application is the U.S. National Phase application under 35 U.S.C. § 371 of International Application Serial No. PCT/EP2018/065580, filed on 13 Jun. 2018, which claims the benefit of U.S. application Ser. No. 62/520,102, filed on 15 Jun. 2017 and European Application Serial No. 17187349.0, filed on 22 Aug. 2017. These applications are hereby incorporated by reference herein.

BACKGROUND

1. Field

The present disclosure pertains to a system and method for reducing physiological data size, including, for example, encoding and/or decoding brain activity signals associated with a sleep session to reduce a size of data representative of the brain activity signals.

2. Description of the Related Art

In recent years, a number of consumer sleep technologies ("CST") have emerged on the market, some which rely on electroencephalogram ("EEG") signals, to enable individuals to monitor their sleep. Although such technologies exist to obtain an individual's EEG or other physiological signals for sleep monitoring, the substantial size of the data (representative of the physiological signals) derived by typical sleep monitoring systems based on the physiological signals collected during one or more sleep sessions make effective and efficient sleep monitoring difficult, if not impractical, to implement. These and other drawbacks exist.

SUMMARY

Accordingly, one or more aspects of the present disclosure relate to a method for reducing a data size of user data associated with a sleep session. The method includes receiving, from one or more sensors, first user data associated with a first sleep session of a user. A determination is made that the first user data includes at least a first instance of a first sleep feature, the first sleep feature being a first data size. A first value representing the first instance during a first temporal interval is determined. First encoding data representing the first value is determined, the first encoding data being a second data size that is less than the first data size. Second user data is then generated by encoding the first user data using the first encoding data to represent the first instance in the second user data, and the second user data is stored.

Another aspect of the present disclosure relates to a system for reducing a data size of user data associated with a sleep session. The system includes one or more sensors, memory, and one or more processors configured by machine-readable instructions stored by the memory to receive, from the one or more sensors, first user data associated with a first sleep session of a user. The one or more processors are further configured by the machine-readable instructions to determine that the first user data includes at least a first instance of a first sleep feature, the first sleep feature being a first data size. The one or more processors are further configured by the machine-readable instructions to determine a first value representing the first instance during a first temporal interval. The one or more processors are further configured by the machine-readable instructions to determine first encoding data representing the first value, the first encoding data being a second data size that is less than the first data size. The one or more processors are further configured by the machine-readable instructions to generate second user data by encoding the first user data using the first encoding data to represent the first instance in the second user data, and to store the second user data.

Yet another aspect of the present disclosure relates to a system for reducing a data size of user data associated with a sleep session. The system includes means for receiving, from one or more sensors, first user data associated with a first sleep session of a user, means for determining that the first user data includes at least a first instance of a first sleep feature, the first sleep feature being a first data size, means for determining a first value representing the first instance during a first temporal interval, means for determining first encoding data representing the first value, the first encoding data being a second data size that is less than the first data size, means for generating second user data by encoding the first user data using the first encoding data to represent the first instance in the second user data, and means for storing the second user data.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

BRIEF DESCRIPTION OF THE DRAWINGS

FIG. 4 is an illustrative diagram of a table of entropy values for various sleep features, in accordance with various embodiments;

DETAILED DESCRIPTION OF EXEMPLARY EMBODIMENTS

Figure 1A:
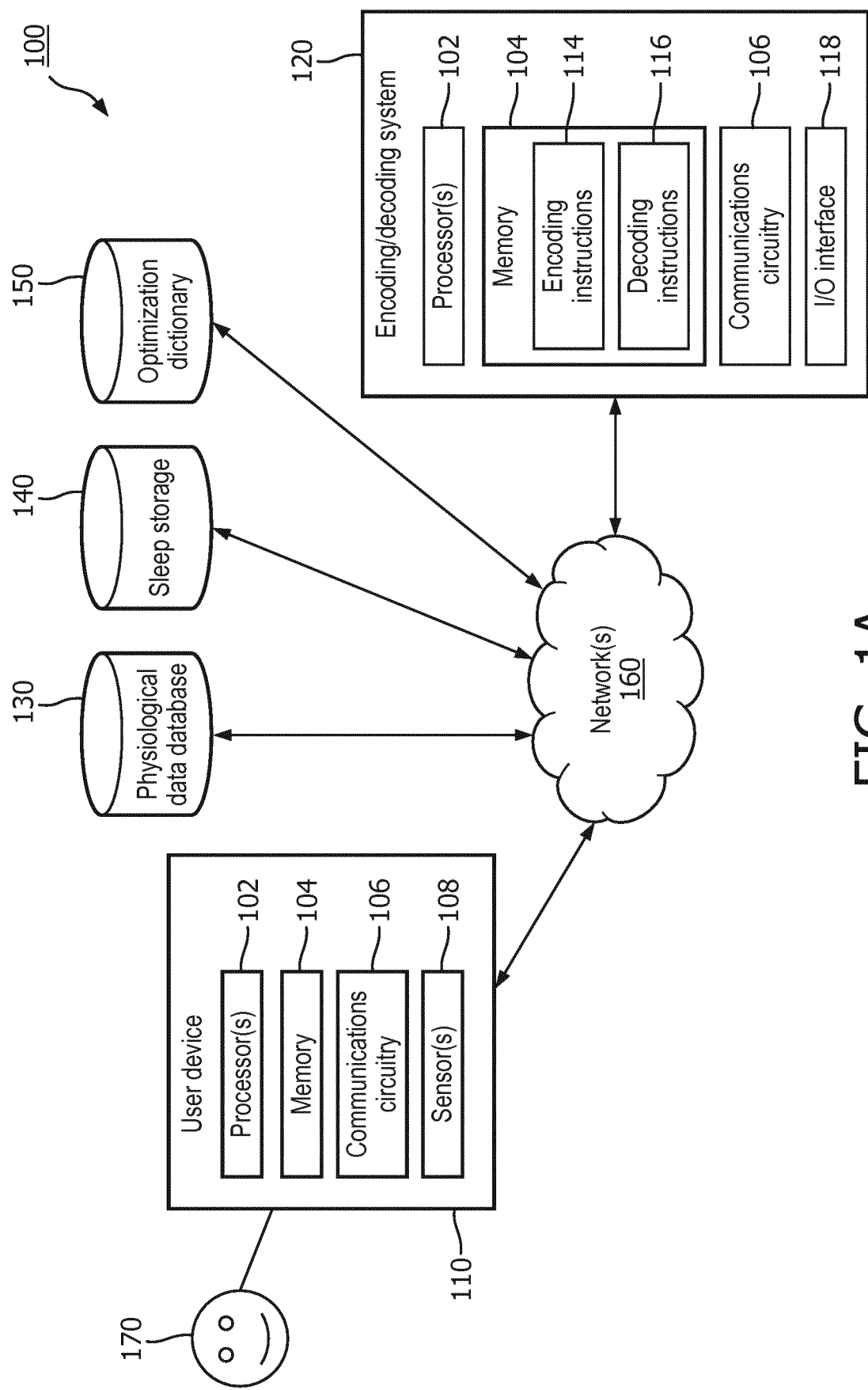
FIG. 1A is a schematic illustration of an exemplary system configured to reduce physiological data size, in accordance with various embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1A is a schematic illustration of an exemplary system 100 configured to reduce physiological data size, in accordance with various embodiments. System 100, in a non-limiting embodiment, includes a user device 110 and an encoding/decoding system 120. User device 110 and encoding/decoding system 120 are capable of communicating with one another via one or more network(s) 160. For example, user device 110 and encoding/decoding system 120 may communicate over an intranet and/or the Internet. Furthermore, in one embodiment, system 100 includes a physiological data database 130, sleep storage 140, and an optimization dictionary 150.

In the illustrative embodiment, user device 110 is configured to monitor brain signals of a user 170 detected using one or more sensors 108 during a sleep session. Although sensor(s) 108 is depicted as being a part of user device 110, it is understood that, in some embodiments, sensor(s) 108 may be a component separate from user device 110 and/or a part of another component of system 100. Sensor(s) 108 correspond to any suitable sensor capable of measuring one or more parameters of user 170. For example, sensor(s) 108 may correspond to one or more EEG devices, as described in greater detail below with reference to FIG. 1B. As another example, sensor(s) 108 may also correspond to one or more accelerometers, one or more gyroscopes, one or more pulse rate monitors, and/or one or more breath monitoring devices. However, persons of ordinary skill in the art will recognize that user device 110 may include any additional type of sensor, or any combination thereof.

In the example embodiment where sensor(s) 108 correspond to EEG sensors, brain signals monitored during sleep can, if stored, accumulate of the order of 100 MB of data per channel for sleep relevant features. Typically, EEG monitoring sleep features include power in such frequency bands as the alpha band (e.g., 8-12 Hz), beta band (e.g., 15-30 Hz), delta band (e.g., 0.5-4 Hz), density of detected slow-waves, and sleep depth (e.g., a ratio between delta and beta).

The various dynamics of the sleep process, such as, and without limitation, a duration of the NREM/REM cycle, and/or variation in sleep depth, are able to be used to define a relevance sampling that sub-samples the feature's time series. As an illustrative example, raw EEG signals may be sampled at a frequency of 100 Hz, but sleep depth value may be sampled at 1 sample per minute with minor loss of information. In one embodiment, sensor(s) 108 are configured to take measurements at predefined temporal intervals. For instance, sensor(s) 108 may be configured (e.g., by processor(s) 102 using instructions stored by memory 104) to take a "sample" measurement every second. A sampling rate how often sensor(s) 108 take a measurement is configurable by user device 110 and can depend on a type of sensor that sensor(s) 108 correspond to, as well as a type of measurement that sensor(s) 108 is attempting to obtain. Furthermore, sensor(s) 108 are capable of being configured by user 170 and/or by one or more other devices of system 100 (e.g., user device 110, encoding/decoding system 120) to modify a sample rate for sensor(s) 108 depending on a particular functionality desired.

In one embodiment, a dictionary of values is stored for each sleep feature, where each value is configured to maximize a ratio of information content to size. Quantizing these values allows regions, within the spaces of values for the corresponding sleep feature, to be defined such that coding is able to be performed in a few bits of data. For instance, sixteen regions may require 4 bits per sample, while eight regions may require 3 bits per sample. As an illustrative example, an eight (8) hour long EEG signal collected during a sleep session of user 170 by sensor(s) 108, where sensor(s) 108 is/are configured to sample at a frequency of 100 Hz with a 16 bit per sample ratio would require approximately 10 MB of storage space. As another example, if a sleep feature requiring 4 bits per sample at a sampling rate of one sample per minute was employed, this would only require 240 bits of storage space. Comparing these two examples indicates that reduction in the sampling rate and bit/sample ratio can produce a data reduction upwards of $10^{-4}$.

User device 110, in one embodiment, corresponds to any suitable type of electronic device including, but are not limited to, desktop computers, mobile computers (e.g., laptops, ultrabooks, etc.), mobile phones, smart phones, tablets, personal digital assistants ("PDAs"), and/or wearable devices (e.g., watches, pins/broaches, headphones, etc.). Furthermore, in the illustrative embodiment, user device 110 includes one or more processors 102, memory 104, and communications circuitry 106.

Encoding/decoding system 120, furthermore, in one embodiment, corresponds to any suitable type of electronic device including, but are not limited to, desktop computers, mobile computers (e.g., laptops, ultrabooks, etc.), mobile phones, smart phones, tablets, personal digital assistants ("PDAs"), and/or wearable devices (e.g., watches, pins/broaches, headphones, etc.). Furthermore, in the illustrative embodiment, user device 110 includes one or more processors 102, memory 104, and communications circuitry 106.

In one embodiment, both user device 110 and encoding/decoding system 120 are similar to one another. For example, user device 110 may correspond to a mobile phone (e.g., a smart phone), while encoding/decoding system 120 may correspond to a tablet. As another example, user device 110 may correspond to a particular EEG sleep monitoring device, whereas encoding/decoding system 120 may correspond to a mobile device (e.g., a smart phone, tablet, etc.). Persons of ordinary skill in the art will further recognize that any other type of electronic device is contemplated as being used within the scope of the present teachings, and the aforementioned is merely exemplary.

Processor(s) 102 include any suitable processing circuitry capable of controlling operations and functionality of user device 110, as well as facilitating communications between various components within user device 10. In one embodiment, processor(s) 102 may include a central processing unit ("CPU"), a graphic processing unit ("GPU"), one or more microprocessors, a digital signal processor, or any other type of processor, or any combination thereof. In another embodiment, the functionality of processor(s) 102 is performed by one or more hardware logic components including, but not limited to, field-programmable gate arrays ("FPGA"), application specific integrated circuits ("ASICs"), application-specific standard products ("ASSPs"), system-on-chip systems ("SOCs"), and/or complex programmable logic devices ("CPLDs"). Furthermore, each of processor(s) 102 is capable of including its own local memory, which may store program systems, program data, and/or one or more operating systems. However, processor(s) 102 are capable of running an operating system ("OS") for user device 110, and/or one or more firmware applications, media applications, and/or applications resident thereon. In one example embodiment, processor(s) 102 runs a local client script for reading and rendering content received from one or more websites. For example, processor(s) 102 may run a local JavaScript client for rendering HTML or XHTML content.

Memory 104, in one embodiment, includes one or more types of storage mediums such as any volatile or non-volatile memory, or any removable or non-removable memory implemented in any suitable manner to store data for user device 110. For example, information may be stored using computer-readable instructions, data structures, and/or program systems. Various types of storage/memory may include, but are not limited to, hard drives, solid state drives, flash memory, permanent memory (e.g., ROM), electronically erasable programmable read-only memory ("EEPROM"), CD-ROM, digital versatile disk ("DVD") or other optical storage medium, magnetic cassettes, magnetic tape, magnetic disk storage or other magnetic storage devices, RAID storage systems, or any other storage type, or any combination thereof. Furthermore, memory 104 may be implemented as computer-readable storage media ("CRSM"), which may be any available physical media accessible by processor(s) 102 to execute one or more instructions stored within memory 104. In an example embodiment, one or more applications (e.g., gaming, music, video, calendars, lists, etc.) are run by processor(s) 102, and may be stored in memory 104.

Communications circuitry 106, in one embodiment, corresponds to any circuitry allowing or enabling one or more components of user device 110 to communicate with one another, and/or with one or more additional devices, servers, and/or systems (e.g., encoding/decoding system 120). As an illustrative example, user data corresponding to readings obtained by sensor(s) 108 may be transmitted over a network 160, such as the Internet, to encoding/decoding system 120 using any number of communications protocols. For example, network(s) 160 are capable of being accessed using Transfer Control Protocol and Internet Protocol ("TCP/IP") (e.g., any of the protocols used in each of the TCP/IP layers), Hypertext Transfer Protocol ("HTTP"), WebRTC, SIP, and wireless application protocol ("WAP"), are some of the various types of protocols that may be used to facilitate communications between user device 110 and encoding/decoding system 120. In one embodiment, user device 110 and/or encoding/decoding system 120 communicate with one another via a web browser using HTTP. Various additional communication protocols used to facilitate communications between one or more devices of system 100 include, but not limited to, Wi-Fi (e.g., 802.11 protocol), Bluetooth, radio frequency systems (e.g., 900 MHz, 1.4 GHz, and 5.6 GHz communication systems), cellular networks (e.g., GSM, AMPS, GPRS, CDMA, EV-DO, EDGE, 3GSM, DECT, IS-136/TDMA, iDen, LTE or any other suitable cellular network protocol), infrared, BitTorrent, FTP, RTP, RTSP, SSH, and/or VOIP. Communications circuitry 106 is capable of using communications protocol, such as any of the previously mentioned exemplary communications protocols. In one embodiment, user device 110 includes one or more antennas to facilitate wireless communications with a network using various wireless technologies (e.g., Wi-Fi, Bluetooth, radiofrequency, etc.). In yet another embodiment, user device 110 includes one or more universal serial bus ("USB") ports, one or more Ethernet or broadband ports, and/or any other type of hardwire access port so that communications circuitry 106 allows user device 110 to communicate with one or more communications networks (e.g., network(s) 160).

As illustrated by FIG. 1A, as user 170 sleeps, user device 110 and/or sensor(s) 108 may monitor sleep activity. In one embodiment, user device 110 (e.g., via sensor(s) 108) is configured to send user data associated with a first sleep session of user 170 to encoding/decoding system 120. For example, user data indicating an activity of user 170 during a first sleep session may be sent to encoding/decoding system 120 via network(s) 160. In one embodiment, the user data is provided to encoding/decoding system 120 at an end of the sleep session. In one embodiment, the user data is provided to encoding/decoding system 120 periodically (e.g., every 5 minutes, every 10 minutes, every half hour, every hour, etc.).

Encoding/decoding system 120, in the non-limiting embodiment, includes processor(s) 102, memory 104, communications circuitry 106, and an I/O (input/output) interface 118. Processor(s) 102, memory 104, and communications circuitry 106 of encoding/decoding system 120 are, in one embodiment, substantially similar to processor(s) 102, memory 104, and communications circuitry 106 of user device 110, and the previous description may apply.

I/O interface 118 is capable of corresponding to any suitable input and/or output component such as, and without limitation, one or more microphones or other audio input devices, one or more speakers or other audio output devices, one or more input mechanisms (e.g., buttons, knobs, switches, etc.), one or more cameras or other image capture devices, and/or one or more display screens. For example, encoding/decoding system 120 may include a display screen of any suitable size and/or shape. Various types of displays include, but are not limited to, liquid crystal displays ("LCD"), monochrome displays, color graphics adapter ("CGA") displays, enhanced graphics adapter ("EGA") displays, variable graphics array ("VGA") display, or any other type of display, or any combination thereof. I/O interface 118 further is capable of including a touch screen, such as a touch screen including capacitive sensing panels capable of recognizing touch inputs thereon. For instance, a touch screen may correspond to a projected capacitive touch ("PCT"), screen include one or more row traces and/or driving line traces, as well as one or more column traces and/or sensing lines.

In the non-limiting embodiment, memory 104 includes instructions for encoding and/or decoding user data associated with a particular sleep session of user 170. As mentioned previously, storing user data associated with a sleep session, such as EEG data representing EEG signals can require a large amount of memory. Therefore, reducing a size of the data while retaining a quality of that data is optimal. Furthermore, being able to extract useful sleep features, and perform useful analysis of a sleep session from a data that has been reduced in size is also necessary. In one embodiment, encoding instructions 114 are associated with one or more rules/instructions for encoding user data associated with a sleep session, and decoding instructions 116 are associated with one or more rules/instructions for decoding additional user data representing a reduced version of user data for a sleep session. Encoding/decoding system 120 is configured to receive the user data associated with a sleep session and determine that the user data includes at least one instance of a first sleep feature, which is of a first size. For example, EEG power in the delta band (Delta RMS), EEG power in the beta band (Beta RMS), EEG power in the alpha band, sleep hypnogram, a range of an EEG signal amplitude, a sleep depth (a ration between delta and beta powers), a time of detected sleep waves, a number of sleep slow waves per unit of time, an impedance, and/or a timing of detected sleep micro-arousals are all exemplary types of features capable of being determined to have occurred during a particular sleep session.

As described in greater detail below, encoding/decoding system 120 is configured, in one embodiment, to determine that the user data includes one or more instances of one or more sleep features. In one embodiment, encoding/decoding system 120 is capable of performing comparisons between user data received from sensor(s) 108 and reference data representing particular sleep features. For instance, system 100 includes, in one embodiment, a physiological data database 130 that stores reference sleep feature data, such as reference EEG data representing particular sleep signals. Encoding/decoding system 120 is configured to access physiological data database 130 via network(s) 160. Additionally, or alternatively, physiological data database 130 may be stored locally within memory 104 of encoding/decoding system 120.

Based on the particular type of sleep feature, a value representing that sleep feature during a first temporal interval is determined, and first encoding data representing that value is determined. In the illustrative embodiment, the sleep feature corresponds to a first data size, whereas the first encoding data is of a second size. The encoding data, in one embodiment, is stored within an optimization dictionary 150, which is accessible by encoding/decoding system 120 via network 160. However, persons of ordinary skill in the art will recognize that some or all of the encoding data (and/or additional information) may be stored locally within memory 104 of encoding/decoding system 120 so as to allow data processing to occur regardless of network connectivity, and the aforementioned is merely illustrative.

Encoding/decoding system 120, in one embodiment, generates second user data by encoding the first user data using the first encoding data to represent the first instance in the second user data. Encoding/decoding system 120 is that configured to store the second user data, either within memory 104 (e.g., locally), or within a sleep storage database 140 accessible via network(s) 160. In a similar spirit, encoding/decoding system 120, in one embodiment, is capable of decoding user data to identify particular sleep features associated with a larger data size.

As mentioned previously, user device 110 is configured to monitor user activity during a sleep session of a user. In one example embodiment, user device 110 and/or sensor(s) 108 are configured to monitor EEG signals during the sleep session. For simplicity, only a single EEG signal, also referred to as a channel, is described, however persons of ordinary skill in the art will recognize that similar descriptions may apply for each channel of user device 110.

Figure 1B:
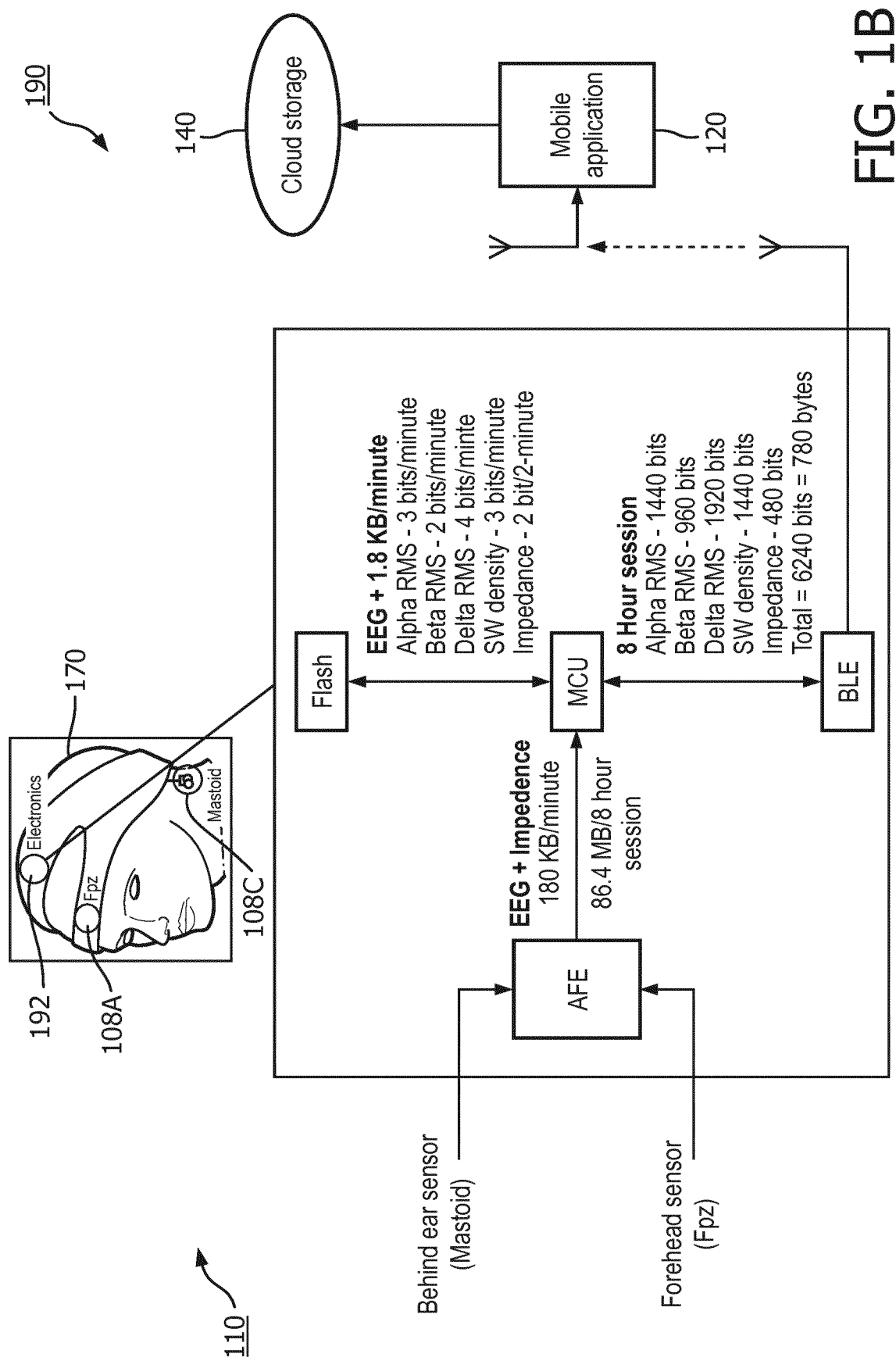
FIG. 1B is an illustrative diagram of an exemplary system including an exemplary user device including one or more sensor(s), in accordance with various embodiment.

FIG. 1B is an illustrative diagram of a system 190 including an exemplary user device 110 including one or more sensor(s), in accordance with various embodiment. In the non-limiting embodiment, user device 110 include a first sensor 108A located at a first position about user 170 and a second sensor 108B located at a second position about user 170. As an illustrative example, first sensor 108A and second sensor 108B may each be configured to measure EEG signals of user 170 while being donned by user 170. Persons of ordinary skill in the art will recognize that user device 110 may include additional sensors, or fewer sensors, and the aforementioned is merely exemplary.

In one embodiment, first sensor 108A corresponds to a forehead sensor, which is configured to reside substantially on a forehead of user 170 when user device 110 is worn by user 170. Second sensor 108B corresponds, in this embodiment, to a behind-the-ear, or mastoid, sensor, which is configured to reside behind, or substantially behind, an ear of user 170 when user device 110 is worn by user 170. In one embodiment, user device 110 also includes electronics such as processors(s) 102, memory 104, and/or communications circuitry 106. For instance, each of processor(s) 102, memory 104, and/or communications circuitry 106 may be capable of being housed by user device 110 at a location 192.

Each of sensors 108A and 108B are configured to capture EEG signals at a particular sampling rate, in one embodiment, in addition to one or more sleep features. For example, an EEG and impedance of a particular channel (e.g., associated with one of sensors 108A and 108B) may monitor EEG signals and impedance, which may be captured thereby. The amount of data that is accumulated by such monitoring accounts for a significant amount of memory. For example, an EEG signal plus impedance may correspond to approximately 180 Kb of data every minute (e.g., 180 Kb/min). Over an eight (8) hour sleep session, this corresponds to approximately 86.4 Mb of data. While sleep storage 140 is, in one embodiment, able to store large amounts of data, storing approximately 100 Mb of data per sleep session (e.g., per day) adds up quickly. As described herein, encoding/decoding system 120 is configured to encode the user data obtained from user device 110 such that the data is reduced in size from of the order of Mbs to Kbs, thereby reducing the data storage requirements by a factor of $10^{-4}$.

Figure 2:
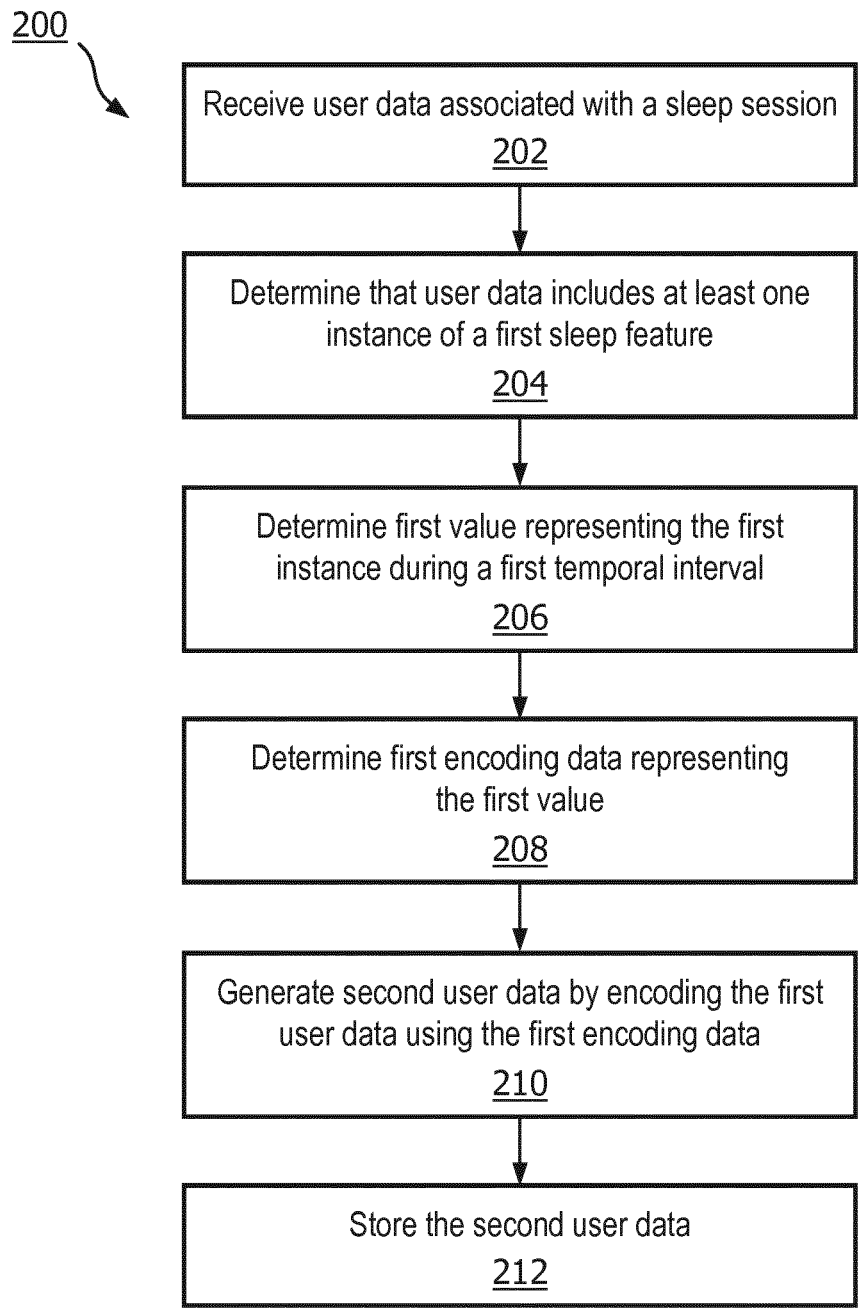
FIG. 2 is an illustrative flowchart of a process for building an optimization dictionary, in accordance with various embodiments.

FIG. 2 is an illustrative flowchart of a process 200 for building an optimization dictionary 150, in accordance with various embodiments. Process 200, in a non-limiting embodiment, begins at operation 202. At operation 202, user data associated with a first sleep session is received. For example, user data obtained by sensor(s) 108 of user device 110 during a first sleep session of user 170 may be sent to encoding/decoding system 120. In one embodiment, in response to receiving the user data, encoding/decoding system 120 generates and sends a request to physiological data database 130 to obtain reference EEG data to be used to compare with user data associated with a first sleep session of user 170. The request may be sent by encoding/decoding system 120 to physiological data database 130 via network(s) 160, and the reference EEG data may in turn be provided to encoding/decoding system 120 via network(s) 160.

At operation 204, encoding/decoding system 120 determines that the user data includes at least a first instance of a first sleep feature. For instance, certain characteristics of an EEG signal may reflect a particular sleep feature such as, and without limitation, Delta RMS, Beta RMS, EEG power in the alpha band, sleep hypnogram, EEG running average, ration of delta and beta powers, timing of detected sleep waves, a number of sleep slow waves per unit of time, an impedance, and/or a timing of detected sleep micro-arousals. The reference EEG data obtained from physiological data database 130, in the example embodiment, includes data representing one or more of these sleep features. A comparison may then be performed between the reference EEG data and the user data to determine whether the user data includes any of these sleep features. In one embodiment, the sleep features mentioned above are, typically, of a first data size, as described in greater detail below with reference to FIG. 3.

To perform the comparison, the user data is compared with one or more reference EEG data and a confidence score is determined indicating a likelihood that the user data includes a particular sleep feature being analyzed for. If the confidence score is greater than a threshold confidence score value, then encoding/decoding system 120 identifies the user data as including that sleep feature. In one embodiment, the user data is segmented into temporal intervals, which may be discrete or overlapping. User data corresponding to each temporal interval is, therefore, compared to the reference EEG data to determine if a sleep feature occurred during that temporal interval. In one embodiment, the user data includes temporal metadata indicating a time during which particular EEG signals were obtained by sensor(s) 108.

At operation 206, a first value representing the first instance during a first temporal interval is determined. The first value corresponds to a sleep-related informative value associated with the particular type of sleep feature that the first instance is associated with. The first value is determined by the extent with which the sleep signal associated with the first instance is able to be reconstructed from stored information (e.g., reference EEG data stored by physiological data database 130 and/or data stored by sleep storage 140), as described in greater detail below with reference to FIG. 3. Generally speaking, the first value indicates a data size associated with that sleep feature prior to encoding being performed.

Figure 3:
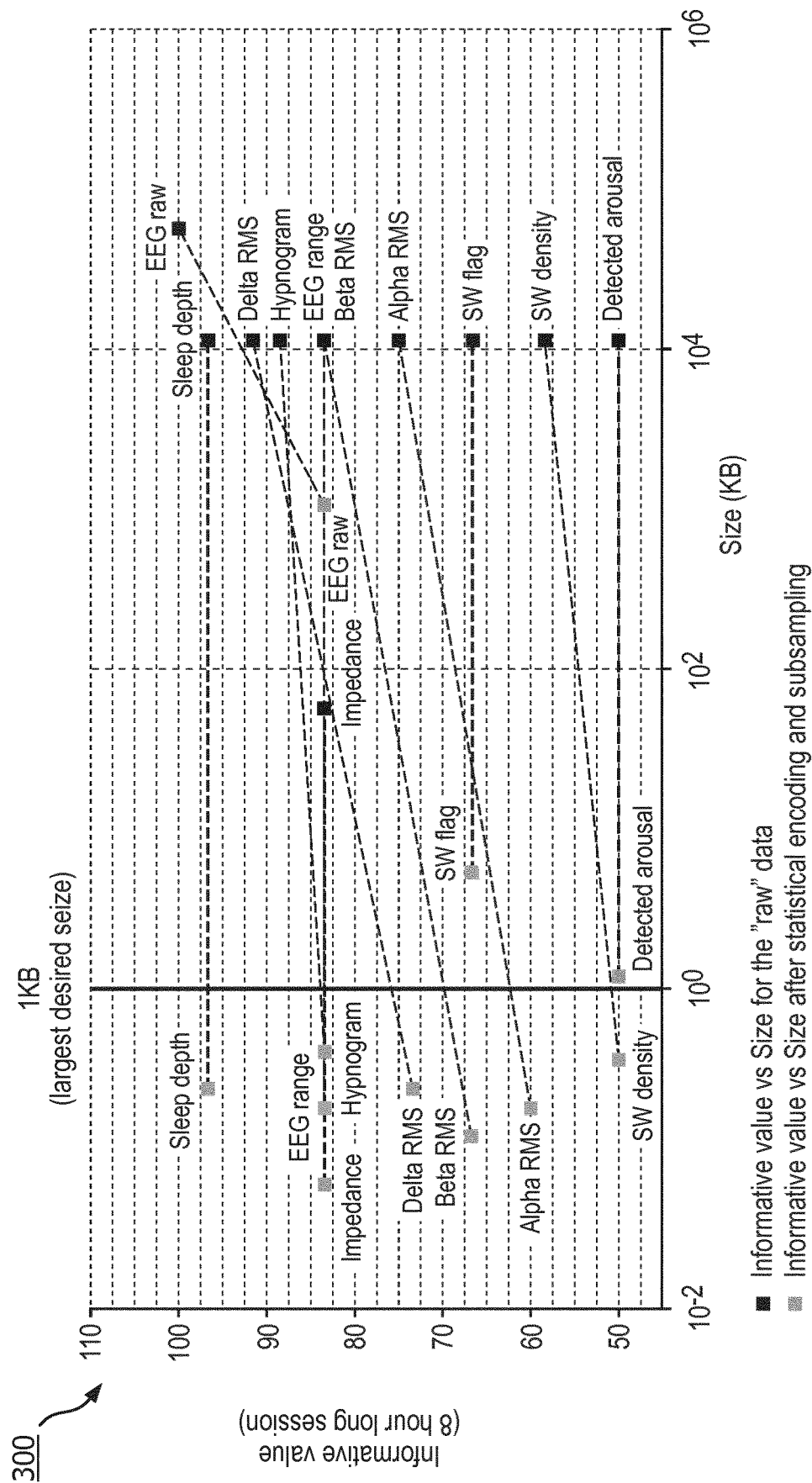
FIG. 3 is an illustrative graph indicating informative values of various sleep features compared to data size, in accordance with various embodiments.

FIG. 3 is an illustrative graph 300 indicating informative values of various sleep features compared to data size, in accordance with various embodiments. As seen within graph 300, various a data size of various sleep features prior to any encoding being performed is displayed by the right-most, black, data points. As an illustrative example, the raw user data associated with a raw EEG signal may have an informative value of approximately 100 for a sleep session lasting approximately eight hours and a data size of greater than $10^4$ Kb. As another illustrative example, the raw user data associated with a detected arousal signal may have an informative value of approximately 50 for an eight hour sleep session, and a data size of approximately $10^4$ Kb.

Information content is estimated for each feature included within graph 300. To do this, for instance, entropy applied to an empirical distribution for that feature is used. The entropy, in one embodiment, is represented via Equation 1:

$$\Sigma_{i=1}^{n} p_i \log_2(p_1)$$   Equation 1.

A histogram for each of the sleep features is then able to be determined using a database of sleep recordings to estimate that sleep feature's corresponding entropy, as described by Equation 1. Exemplary entropy values are show in greater detail within FIG. 4.

FIG. 4 is an illustrative diagram of an exemplary table 400 of entropy values for various sleep features, in accordance with various embodiments. As seen by table 400, entropy, in one embodiment, also corresponds to a number of bits per sample for each sleep feature. For example, the sleep feature impedance may have an entropy, or bits per sample, value of 1.7.

The number of regions with which a particular sleep feature is to be quantized into is based on the values identified within table 400. Using these values, the quantization is capable of being performed to indicate the values that will be used to encode each region. In one non-limiting embodiment, these values, defining the encoding stored by optimization dictionary 150, are indicated below with reference to Table 1.

TABLE 1

| Alpha [uV] | Beta [uV] | Delta [uV] | Impedance | Slow-wave density [Slow waves/second] |
|---|---|---|---|---|
| 2.1389 | 1.0534 | 1.8934 | 367.3564 | 0.2099 |
| 3.5367 | 1.3904 | 6.2918 | 497.6230 | 1.5587 |
| 5.1128 | 1.8366 | 9.8558 | 669.0929 | 3.1448 |
| 8.1437 | 2.5270 | 13.7817 | 913.3683 | 4.9673 |
| 12.5683 | 3.4515 | 18.4656 | 1299.1674 | 7.2324 |
| 19.0424 | 4.7998 | 24.2372 | 1884.4842 | 9.7197 |
| 31.6328 | 6.3910 | 31.8331 | 2549.3589 | 12.5771 |
| 43.7197 | 8.5267 | 43.0125 | 2760.7558 | 15.5912 |

As seen by Table 1, exemplary encoding values for various sleep features are described. The impedance values are related to an impedance in Ohms by a polynomial regression equation. The encoding values correspond to sleep features such as alpha, beta, delta, impedance, and slow-wave density, however persons of ordinary skill in the art will recognize that additional, alternative, and/or fewer values may be included, and the aforementioned is merely exemplary. Each of the alpha, beta, and delta units corresponds to power in root-means-square ("RMS") units (e.g., µV). For instance, signals are filtered in a particular frequency band of interest (e.g., for alpha, 8-12 Hz), which is squared on a per-sample basis and then averaged using a running average window (e.g., 1 second for alpha, 1 second for beta, and 10 seconds for delta), which is then squared to yield the final result listed above.

Each value of Table 1 is associated with unique encoding data. Therefore, the first value representing the first instance of the sleep feature during a first temporal interval of the sleep session is compared with the dictionary values stored within Table 1 to determine the corresponding encoding data that represents it. In a non-limiting embodiment, Table 1 includes, for each sleep feature, eight values. Therefore, encoding data representing a three bit value is used to identify the particular dictionary value that the first value corresponds to. For example, a first dictionary value for alpha (e.g., 2.1389) may be represented by the binary code 000, a second dictionary value may be represented by 001, etc. Comparison between the first value representing the first instance of the sleep feature for a given temporal interval may be mapped to the dictionary value to see which dictionary value is closest to the first value. In one embodiment, if the first value representing the first instance is greater than a first dictionary value, but less than or equal to a second dictionary value, then encoding data representing the first dictionary value may be used to describe the first value. For example, if the first value representing the first instance of an alpha sleep feature within the user data is 2.2, then the encoding data representing that value may be the three bit code 000. However, persons of ordinary skill in the art will recognize that any suitable encoding scheme may be employed, and the use of a three bit encoding representation is merely exemplary. Furthermore, the mapping of sleep feature values to encoding data is also amenable to the specific features of the system. If, for instance, there are sixteen dictionary values for a certain sleep feature, then a four bit code may be used instead of a three bit code. The process of determining the encoding data representing the particular value of the instance in the sleep session is described in greater detail below with reference to FIG. 5.

Returning to FIG. 2, process 200 proceeds to operation 208. At operation 208, first encoding data representing the first value is determined. The first encoding data is determined based on the first value with respect to the dictionary values associated with that particular sleep feature. The first encoding data has a data size that is smaller than that of the data size of the first sleep feature. For instance, as seen in FIG. 3, the encoded version of the sleep depth is of the order of 1 Kb in size, whereas the raw version of the sleep depth feature is of the order of $10^4$ Kb. Therefore, by identifying the dictionary value associated with the value representing each instance of a particular sleep feature within user data greatly reduces the overall amount of data storage required to store user data representing a sleep session's sleep features.

At operation 210, second user data is generated by encoding the first user data using the first encoding data to represent the first instance in the second user data. In one embodiment, generating the second user data corresponds to generating each encoded representation of each instance of a particular sleep feature during the various temporal intervals of the sleep session's duration. This yields data representative of each sleep feature's intensity during the sleep session, which is of significantly less data size than that of the raw user data obtained from sensor(s) 108. This process is described in greater detail below with reference to FIG. 6.

At operation 212, the second user data is stored by sleep storage 140. In one embodiment, encoding/decoding system 120 provides the second user data to sleep storage 140 via network(s) 160. However, in one embodiment, encoding/decoding system 120 also, or alternatively, stores the second user data within memory 104. The reduction in data size of the second user data relative to the first user data allows the storage medium (e.g., memory 104 and/or storage system 140) to store significantly more sleep session information, while also retaining the qualitative aspects of the raw sleep session signals captured by sensor(s) 108.

Figure 5:
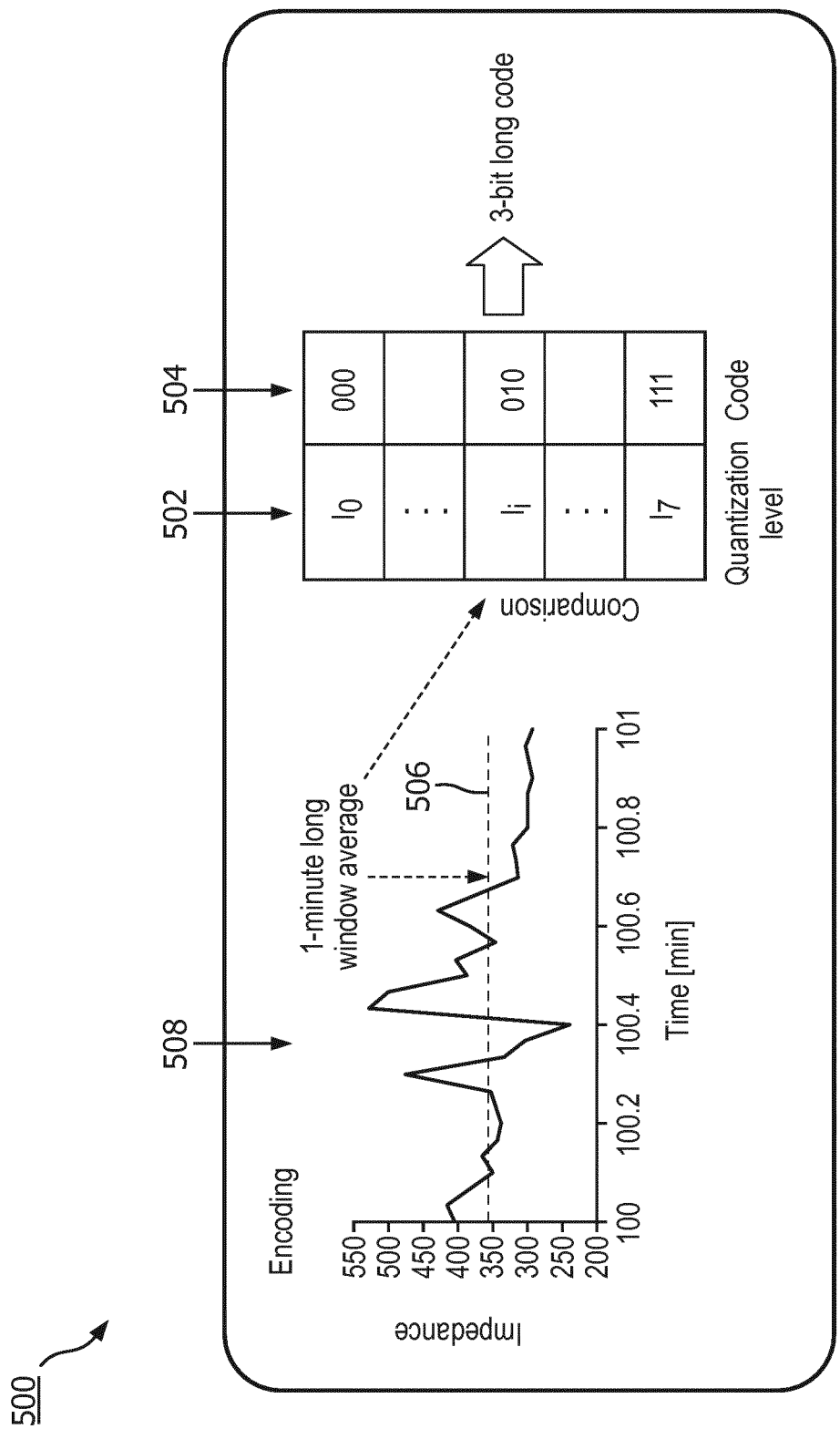
FIG. 5 is an illustrative diagram for determining encoding data representing a first value of a first instance of a sleep feature during a first temporal interval, in accordance with various embodiments.

FIG. 5 is an illustrative diagram 500 for determining encoding data representing a first value of a first instance of a sleep feature during a first temporal interval, in accordance with various embodiments. As seen in diagram 500, a one minute long moving average of a first sleep feature (e.g., impedance) is presented within graph 508. Persons of ordinary skill in the art will recognize that any suitable temporal interval may be employed, and segmentation of the raw user data into one minute temporal intervals is merely exemplary. For instance, a one minute moving average may be employed for an encoding sampling frequency of one sample per minute.

Encoding/decoding system 120, in one embodiment, determines an average impedance 506 during the one minute temporal interval in question. For example, as seen within graph 508, during the one minute temporal interval, the average impedance detected by sensor(s) 108 corresponds to a value of 350. After determining the average impedance 506, this value is compared with the various quantization levels 502 defined by dictionary 150 for the particular sleep feature being analyzed, which in this example embodiment is impedance. In one embodiment, seen above with reference to Table 1, there are eight quantization levels associated with the particular sleep feature being analyzed. Each of these quantization levels is associated with a particular three-bit long code 504. Thus, after determining the value representing the first instance of the sleep feature (e.g., the moving average) during the temporal interval, encoding data, such as code 504, representing that value is determined. The result will be that a particular three-bit code, in the illustrative embodiment, is defined as being representative of EEG signals (or any other type of sensor output being monitor by sensor(s) 108) captured during that temporal interval. This process is able to be repeated by encoding/decoding system 120 for each temporal interval of the sleep session to build a complete mapping of three-bit codes representing the entire sleep session.

In one embodiment, the comparison of the average value during the particular temporal interval being analyzed and the various quantization levels for that sleep feature is performed by encoding/decoding system 120 using encoding instructions 114. For instance, the average value may be compared with each quantization level to determine a difference, or a similarity score, associated with that quantization level. If a particular quantization level's similarity score is greater than or equal to a similarity score threshold, for example, then this may indicate that there is a strong likelihood that that quantization level is represented during the temporal interval. In one embodiment, the similarity score compares a difference between the average value and an upper bound of the quantization level to see if the difference is less than or equal to a particular threshold value. If so, then this indicates that the quantization level represents the average value. In another embodiment, similarity scores for each quantization level are determined by calculating a difference between the average value and a mid-point value for the quantization levels. The quantization level whose difference is smallest as compared to the other differences may, in one embodiment, be identified as representing the average value. However, persons of ordinary skill in the art will recognize that any other suitable criteria for comparing the value (e.g., average value) associated with the temporal interval and a value associated with each quantization level may be employed, and the aforementioned are merely exemplary. After identifying the appropriate quantization level, corresponding encoding data (e.g., a three bit long code) representing that quantization level's value, is identified. Each quantization level, in one embodiment, includes unique encoding data such that that particular quantization level is unable to map to a different representation of the sleep feature.

Figure 6:
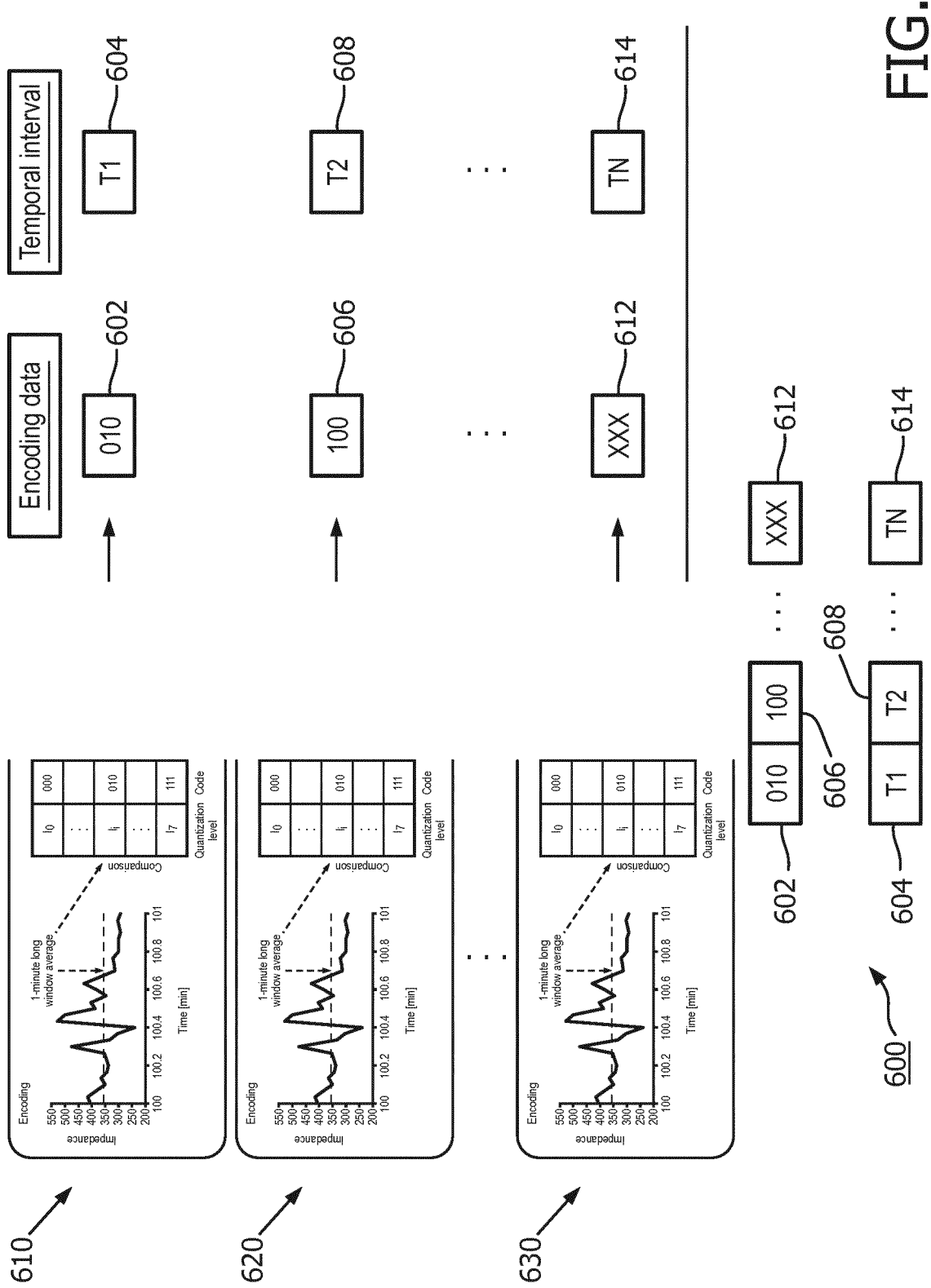
FIG. 6 is an illustrative diagram for generating user data by encoding user data obtained from sensor(s) of user device using encoding data, in accordance with various embodiments.

FIG. 6 is an illustrative diagram for generating user data 600 by encoding user data obtained from sensor(s) 108 of user device 110 using encoding data, in accordance with various embodiments. As seen from FIG. 6, encoding processes 610, 620, and 630 are described from various temporal intervals. The user data, in one embodiment, received from sensor(s) 108 is segmented into temporal intervals each of a particular temporal duration (e.g., one minute), and the encoding process described above with reference to FIG. 5 is performed.

For each temporal interval, encoding data representing a value associated with the instance of the sleep feature determined to be included within the raw user is determined. For instance, encoding process 610 determines that, during temporal interval 604, the value of the instance of the sleep feature identified corresponds to a first quantization level. This quantization level is represented by encoding data 602. Similarly, encoding process 620 determines that, during temporal interval 608, the value of the instance of the sleep feature identified corresponds to a first quantization level, represented by encoding data 606. Still further, encoding process 630 determines that, during temporal interval 614, the value of the instance of the sleep feature identified corresponds to a first quantization level, represented by encoding data 612.

The net result of each of encoding processes 610, 620, and 630, for instance, is user data 600, including each of encoding data 602, 606, and 612, arranged temporally in view of temporal intervals 604, 608, and 614. In one embodiment, each of encoding data 602, 606, and 612 is appended to include temporal metadata indicating the corresponding temporal interval 604, 608, and 614 associated therewith. However, person of ordinary skill in the art will recognize that this is merely exemplary. For example, user data 600 may alternatively be arranged as a string of characters (e.g., three bits having values of one (1) or (0)), which in turn are temporally segmented by the number of characters used to represent the value for that feature (e.g., three characters for a three bit code). This allows for user data 600 to be "decoded," as described in greater detail below with reference to FIG. 7.

Figure 7:
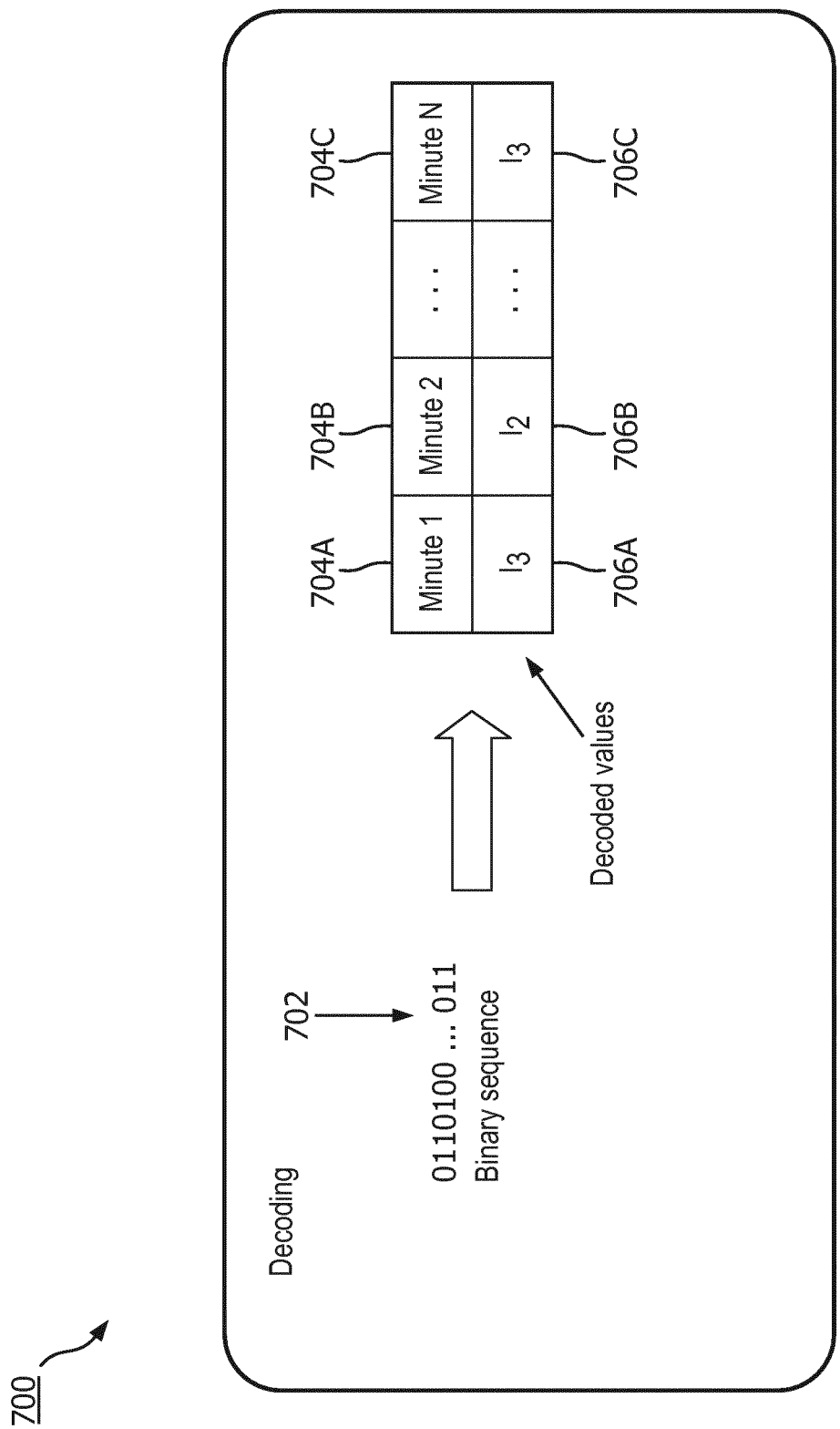
FIG. 7 is an illustrative diagram of a process for decoding user data, in accordance with various embodiments.

FIG. 7 is an illustrative diagram of a process 700 for decoding user data, in accordance with various embodiments. User data 702, which in the illustrative non-limiting embodiment corresponds to user data that has been encoded, is also capable of being decoded using encoding/decoding system 120. To do this, user data 702 is parsed by a number of bits associated with the encoding data. For example, if the encoding data used three-bit long code to encode the user data, then user data 702 will be parsed into three-bit long strings. Each three-bit long string, therefore, is associated with one temporal interval of the sleep session's duration.

In one embodiment, user data 702 is parsed such that the three-bit long strings are arranged in temporal order. For example, the first three bits may correspond to temporal interval 704A, the second three bits may correspond to temporal interval 704B, and the n-th three bits may correspond to temporal interval 704C. By doing this, user data 702 is decomposed into individual sets of encoding data associated with each temporal interval of the sleep session.

After user data 702 has been parsed, encoding data for each temporal interval 704A-C is mapped back to a quantization level of optimization dictionary 150, as described above with reference to Table 1. This allows the representative sleep feature instances occurring during each temporal interval 704A-C to be reconstructed to a high degree of accuracy. In one embodiment, a smoothing filter is also capable of being applied after the decoding process to smooth out the data, however persons of ordinary skill in the art will recognize that this is merely exemplary. The result of the decoding process is, therefore, opposite to the encoding process in that instances of sleep features having a first data size, indicated by the left most points (e.g., the pink points) of graph 300 are able to be reconstructed to their raw data size, as indicated by the right most points (e.g., the black points). This allows for sleep storage 140 (and/or memory 104) to only be required to store data of the order of 1.5 Kbs for an EEG signal of the order of 10 Mbs in data size, for example.

Figure 8:
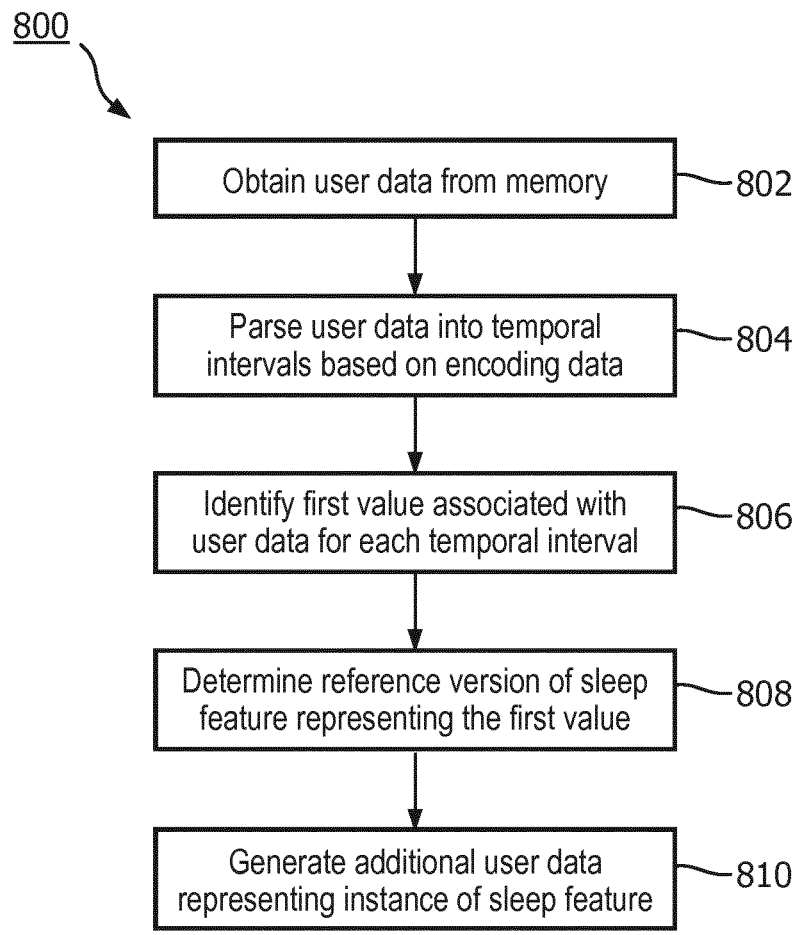
FIG. 8 is an illustrative flowchart of an exemplary process for decoding user data, in accordance with various embodiments.

FIG. 8 is an illustrative flowchart of an exemplary process 800 for decoding user data, in accordance with various embodiments. Process 800, in a non-limiting embodiment, begins at operation 802. At operation 802, user data is obtained from memory. In one embodiment, the user data is obtained by encoding/decoding system 120 from sleep storage 140. Alternatively, or additionally, the user data is obtained from memory 104 of encoding/decoding system 120. In one embodiment, the user data corresponds to user data that has been encoded (e.g., encoded user data 600). The user data is obtained, for instance, in response to a request to analyze user data, which may be generated and sent by encoding/decoding system 120.

At operation 804, the user data is parsed into temporal intervals based on the encoding data. In one embodiment, decoding instructions 116 include instructions for parsing the user data. For example, the user data may indicate a type of encoding that was used to encode that user data. Based on this type of encoding (e.g., three bits long code), the user data is able to be parsed into discrete temporal intervals that encompass a duration of a sleep session with which the user data is associated.

At operation 806, a first value associated with the user data for each temporal interval is identified. For example, based on the three-bit code used to encode a particular temporal interval, a corresponding quantization level associated with that three-bit code may be identified. In one embodiment, dictionary values of optimization dictionary 150 are accessed to determine the corresponding quantization levels associated with the user data for a particular temporal interval.

At operation 808, a reference version of a sleep feature representing the first value is determined. For instance, a reconstructed version of the particular instance of the sleep feature is stored, in one embodiment, by physiological data database 130. Based on the particular value (e.g., the quantization level), that is identified, a reference EEG signal is determined that corresponds to that value.

At operation 810, additional user data representing instances of the sleep feature encoded by the initially obtained user data during for each temporal interval is generated. This is described in greater detail below with reference to FIG. 9. Thus, by encoding the sleep session user data, the same quality of information is able to be retained while reducing a data size of the user data. This improvement is extremely beneficial in that storage systems are able to store much more information and better offline analysis of a user's sleep patterns and behaviors are possible.

Figure 9:
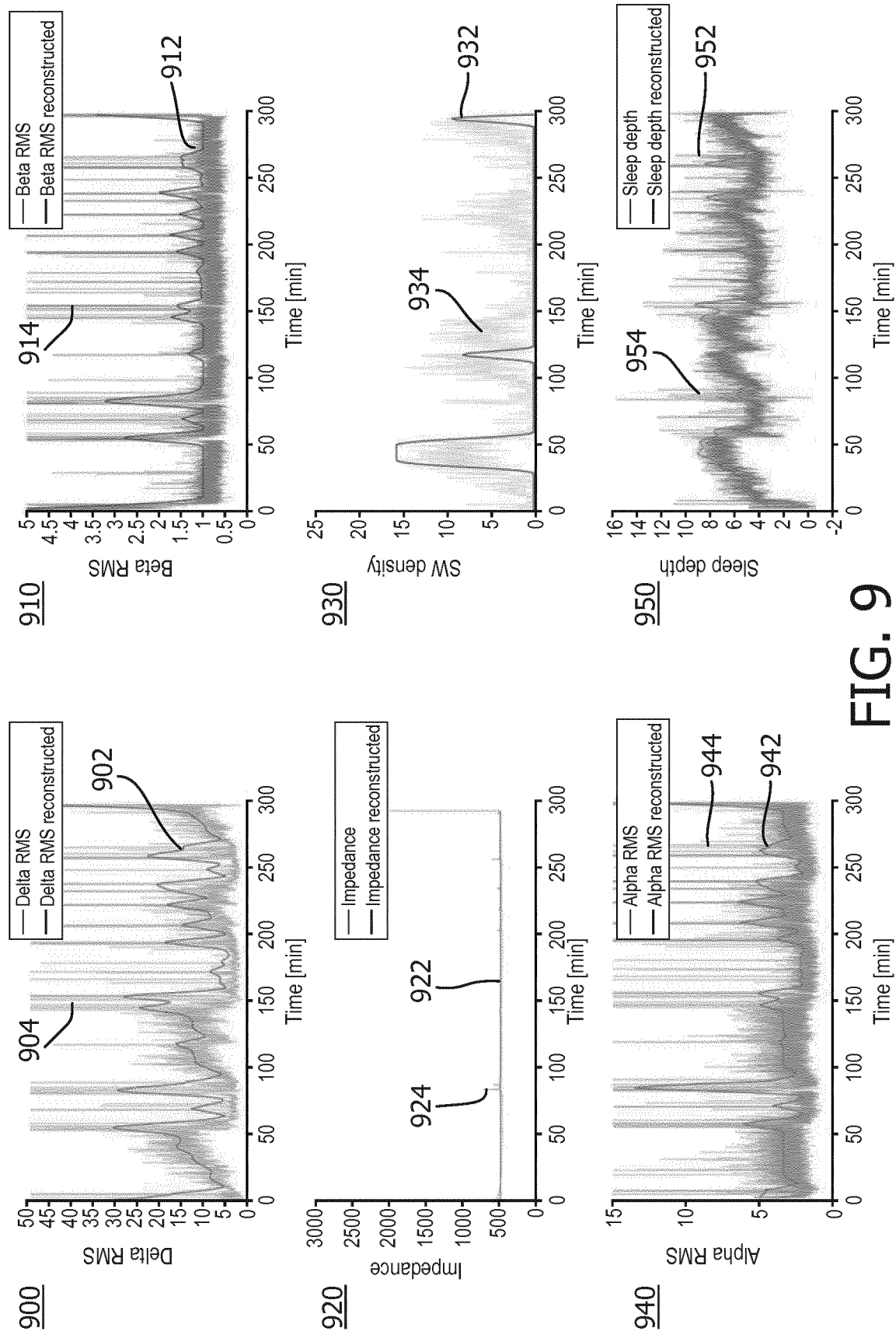
FIG. 9 is an illustrative diagram of various graphs corresponding to various sleep features including both raw user data and reconstructed user data, in accordance with various embodiments.

FIG. 9 is an illustrative diagram of various graphs 900-950 corresponding to various sleep features including both raw user data and reconstructed user data, in accordance with various embodiments. In the illustrative embodiment, graph 900 corresponds to a Delta RMS sleep feature, graph 910 corresponds to a Beta RMS sleep feature, graph 920 corresponds to an impedance sleep feature, graph 930 corresponds to a SW density sleep feature, graph 940 corresponds to an Alpha RMS sleep feature, and graph 950 corresponds to a sleep depth sleep feature.

In each of graphs 900-950, raw sensor data obtained by sensor(s) 108 of user device 110 for a particular sleep feature is displayed. For instance, graph 900 includes raw user data 904, graph 910 includes raw user data 914, graph 920 includes raw user data 924, graph 930 includes raw user data 934, graph 940 includes raw user data 944, and graph 950 includes raw user data 954. As mentioned previously, the raw user data is capable of being encoded to reduce a data size of that user data for improved storage capabilities. In one embodiment, the encoded data may be reconstructed to provide a substantially same quality of information as the raw data. Therefore, each of graphs 900-950 may include reconstructed user data representing the raw user data after it has been encoded and then decoded by encoding/decoding system 120. For instance, graph 900 includes reconstructed user data 902, graph 910 includes reconstructed user data 912, graph 920 includes reconstructed user data 922, graph 930 includes reconstructed user data 932, graph 940 includes reconstructed user data 942, and graph 950 includes reconstructed user data 952. As evident by a comparison between raw data and reconstructed data, the reconstructed user data employing the encoding/decoding techniques described herein provides a substantially accurate recreation of the raw sleep data.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A method for reducing a data size of user data associated with a sleep session, the method comprising:
   for each of a plurality of predetermined sleep features, storing (i) a plurality of quantization levels, and (ii) encoding data corresponding to each of the quantization levels;
   receiving, from one or more sensors, first user data associated with a first sleep session of a user;
   determining that the first user data comprises at least a first instance of a first sleep feature, the first sleep feature being a first data size;
   determining a first value representing the first instance during a first temporal interval;
   determining a particular one of the predetermined sleep features that corresponds to the determined first sleep feature;
   determining a particular one of the quantization levels of the determined particular one of predetermined sleep features that corresponds to the first value;
   determining the encoding data that corresponds to the determined particular one of the quantization levels, the determined encoding data being a second data size that is less than the first data size;
   generating second user data by encoding the first user data using the determined encoding data to represent the first instance in the second user data; and
   storing the second user data.

2. The method of claim 1, further comprising:
   generating, prior to the first value being determined, third user data by applying a first filter to the first user data;
   segmenting the third user data into a plurality of temporal intervals, the plurality comprising the first temporal interval; and
   determining that the first temporal interval comprises the first instance.

3. The method of claim 1, further comprising:
   obtaining the second user data; identifying that the second user data is associated with the first value; and
   generating third user data representing the first value, wherein the third user data comprises a reference version of the first sleep feature.

4. The method of claim 1, wherein receiving the first user data comprising receiving electroencephalogram ("EEG") data, the at least one sleep feature comprises one of: a first amount of EEG power in a delta band RMS, a second amount of EEG power in a beta band RMS, a third amount of EEG power in the alpha band RMS, a sleep hypnogram, a running average associated with the EEG data, a sleep depth, a timing of detected sleep waves, a number of sleep slow waves per unit of time, an impedance, and a timing of detected sleep micro-arousals.

5. The method of claim 1, wherein the first data size corresponds to megabytes of data and the second data size corresponds to kilobytes of data.

6. The method of claim 1, wherein the second user data comprises a three-bit long code representing the first value.

7. A method for reducing a data size of user data associated with a sleep session, the method comprising:
   receiving, from one or more sensors, first user data associated with a first sleep session of a user;
   determining that the first user data comprises at least a first instance of a first sleep feature, the first sleep feature being a first data size;
   determining a first value representing the first instance during a first temporal interval;
   determining first encoding data representing the first value, the first encoding data being a second data size that is less than the first data size;
   generating second user data by encoding the first user data using the first encoding data to represent the first instance in the second user data;
   storing the second user data
   determining, prior to the first value being determined, a sampling rate associated with the first user data;
   generating third user data representing the first user data having the sampling rate being applied to the first user data;
   determining a first entropy rate associated with the first sleep feature; and
   determining that, for a second temporal interval of the third user data, a first feature value corresponds to the first value based on the first feature value being less than a first sleep feature value and greater than a second sleep feature value.

8. A method for reducing a data size of user data associated with a sleep session, the method comprising:
receiving, from one or more sensors, first user data associated with a first sleep session of a user;
determining that the first user data comprises at least a first instance of a first sleep feature, the first sleep feature being a first data size;
determining a first value representing the first instance during a first temporal interval;
determining first encoding data representing the first value, the first encoding data being a second data size that is less than the first data size;
generating second user data by encoding the first user data using the first encoding data to represent the first instance in the second user data;
storing the second user data;
determining that the first user data comprises a second instance of the first sleep feature;
determining a second value representing the second instance occurring during a second temporal interval; and
determining second encoding data representing the second value, the second encoding data being a third data size that is less than the first data size, wherein generating the second user data further comprises encoding the first user data using the second encoding data to represent the second instance in the second user data.

9. The method of claim 8, further comprising:
obtaining the first encoding data and the second encoding data;
obtaining the second user data; identifying that the first encoding data is associated with the first value occurring during the first temporal interval and that the second encoding data is associated with the second value occurring during the second temporal interval; and
generating third user data representing the first value and the second value, wherein the third user data comprises a first reference version of the first value and a second reference version of the second value arranged based on a temporal ordering of the first temporal interval and the second temporal interval.

10. A system for reducing a data size of user data associated with a sleep session, the system comprising:
one or more sensors;
memory including a database, the database, for each of a plurality of predetermined sleep features, storing (i) a plurality of quantization levels, and (ii) encoding data corresponding to each of the quantization levels; and
one or more processors configured by machine-readable instructions to:
receive, from the one or more sensors, first user data associated with a first sleep session of a user;
determine that the first user data comprises at least a first instance of a first sleep feature, the first sleep feature being a first data size;
determine a first value representing the first instance during a first temporal interval;
determine a particular one of the predetermined sleep features that corresponds to the determined first sleep feature;
determine a particular one of the quantization levels of the determined particular one of predetermined sleep features that corresponds to the first value;
determining the encoding data that corresponds to the determined particular one of the quantization levels, the determined encoding data being a second data size that is less than the first data size;
generate second user data by encoding the first user data using the determined encoding data to represent the first instance in the second user data; and
store the second user data.

11. The system of claim 10, wherein the one or more processors are further configured by the machine-readable instructions to:
generate, prior to the first value being determined, third user data by applying a first filter to the first user data;
segment the third user data into a plurality of temporal intervals, the plurality comprising the first temporal interval; and
determine that the first temporal interval comprises the first instance.

12. The system of claim 10, wherein the one or more processors are further configured by the machine-readable instructions to:
obtain the second user data;
identify that the second user data is associated with the first value; and
generate third user data representing the first value, wherein the third user data comprises a reference version of the first sleep feature.

13. The system of claim 10, wherein the first data size corresponds to megabytes of data and the second data size corresponds to kilobytes of data.

14. A system for reducing a data size of user data associated with a sleep session, the system comprising:
one or more sensors;
memory; and
one or more processors configured by machine-readable instructions to:
receive, from the one or more sensors, first user data associated with a first sleep session of a user;
determine that the first user data comprises at least a first instance of a first sleep feature, the first sleep feature being a first data size;
determine a first value representing the first instance during a first temporal interval;
determine first encoding data representing the first value, the first encoding data being a second data size that is less than the first data size;
generate second user data by encoding the first user data using the first encoding data to represent the first instance in the second user data;
store the second user data
determine, prior to the first value being determined, a sampling rate associated with the first user data;
generate third user data representing the first user data having the sampling rate being applied to the first user data;
determine a first entropy rate associated with the first sleep feature; and
determine that, for a first temporal interval of the third user data, a first feature value corresponds to the first value based on the first feature value being less than a first sleep feature value and greater than a second sleep feature value.

* * * * *